United States Patent [19]

Paques

[11] Patent Number: 5,691,312
[45] Date of Patent: Nov. 25, 1997

[54] PHARMACEUTICAL FOR SUBCUTANEOUS OR INTRAMUSCULAR ADMINISTRATION CONTAINING POLYPEPTIDES

[75] Inventor: Eric-Paul Paques, Marburg, Germany

[73] Assignee: Behringwerke Aktiengesellschaft, Marburg, Germany

[21] Appl. No.: 488,952

[22] Filed: Jun. 7, 1995

Related U.S. Application Data

[63] Continuation of Ser. No. 273,621, Jul. 12, 1994, abandoned, which is a continuation of Ser. No. 47,617, Apr. 14, 1993, abandoned, which is a continuation of Ser. No. 742,557, Aug. 9, 1991, abandoned, which is a continuation of Ser. No. 606,312, Oct. 31, 1990, abandoned.

[30] Foreign Application Priority Data

Nov. 29, 1989 [DE] Germany .................. 39 39 346.1

[51] Int. Cl.$^6$ .................. A61K 38/00; A61K 38/16
[52] U.S. Cl. .................. 514/12; 514/8; 514/21; 530/324
[58] Field of Search .................. 514/12, 8, 21; 530/324

[56] References Cited

U.S. PATENT DOCUMENTS

| | | | |
|---|---|---|---|
| 4,327,086 | 4/1982 | Fukushima et al. | 424/177 |
| 4,508,709 | 4/1985 | Amphlett et al. | 530/383 |
| 4,568,544 | 2/1986 | Hasegawa et al. | 424/94 |
| 4,806,524 | 2/1989 | Kawaguchi et al. | 514/8 |
| 4,857,320 | 8/1989 | Wittwer | 424/94.63 |
| 4,992,419 | 2/1991 | Woog et al. | 514/8 |
| 5,068,106 | 11/1991 | Paques et al. | 424/94.3 |
| 5,091,363 | 2/1992 | Heimburger et al. | 514/2 |
| 5,097,019 | 3/1992 | Lobermann et al. | 530/392 |
| 5,358,708 | 10/1994 | Patel | 424/85.1 |
| 5,503,827 | 4/1996 | Woog et al. | 424/85.1 |

FOREIGN PATENT DOCUMENTS

| | | |
|---|---|---|
| 0156169 | 10/1985 | European Pat. Off. . |
| 0292908 | 5/1988 | European Pat. Off. . |
| 0303251 | 2/1989 | European Pat. Off. . |
| 86/06962 | 5/1986 | WIPO . |

OTHER PUBLICATIONS

Yamahira et al. CA vol. 92 No. 13543Q (1980).

*Primary Examiner*—Avis M. Davenport
*Assistant Examiner*—Jennifer Harle
*Attorney, Agent, or Firm*—Finnegan, Henderson, Farabow, Garrett & Dunner, L.L.P.

[57] ABSTRACT

Liquid pharmaceuticals for subcutaneous (sc) or intramuscular (im) administration containing a polypeptide and at least one amino acid, a process for the preparation of such a pharmaceutical and the use of an amino acid, which is suitable for sc or im administration, in a solution of a polypeptide are described.

1 Claim, 2 Drawing Sheets

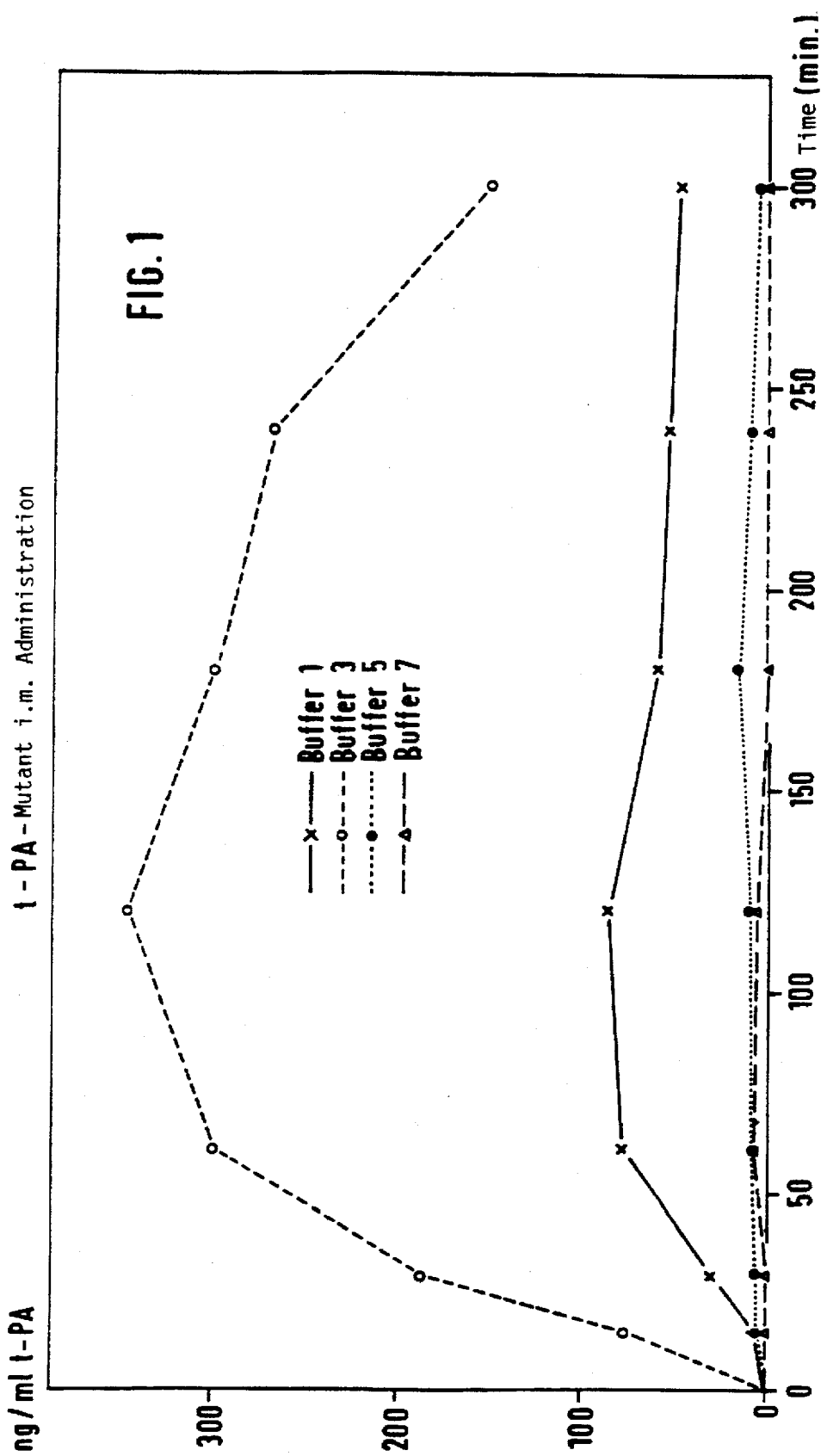

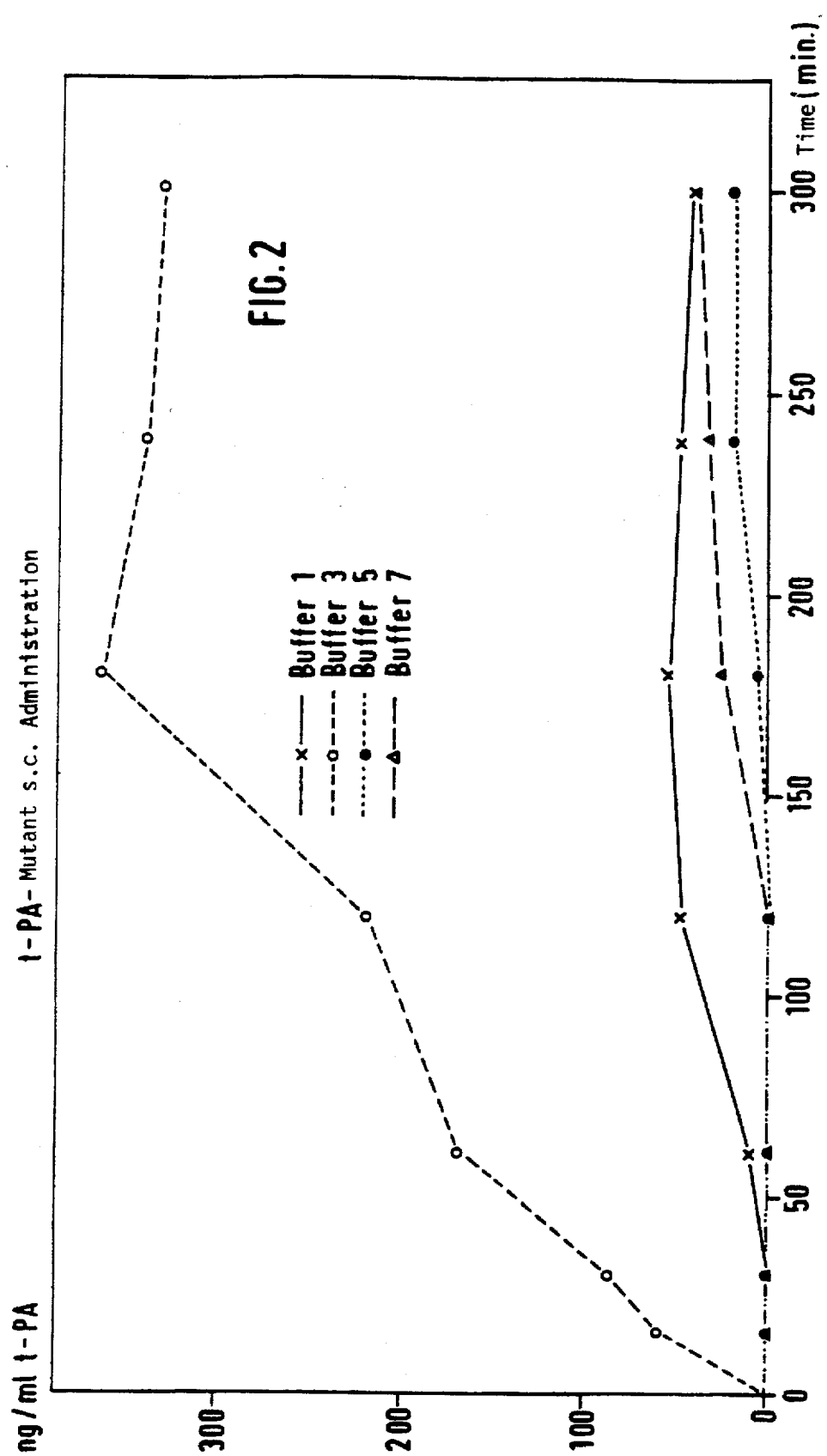

PHARMACEUTICAL FOR SUBCUTANEOUS OR INTRAMUSCULAR ADMINISTRATION CONTAINING POLYPEPTIDES

This application is a continuation of application Ser. No. 08/273,621, filed Jul. 12, 1994, which is a continuation of application Ser. No. 08/047,617, filed Apr. 14, 1993, which is a continuation of application Ser. No. 07/742,557, filed Aug. 9, 1991, which is a continuation of application Ser. No. 07/606,312, filed Oct. 31, 1990, all now abandoned.

The invention relates to a liquid pharmaceutical for subcutaneous (sc) or intramuscular (im) administration containing a polypeptide and at least one amino acid, a process for the preparation of such a pharmaceutical and the use of an amino acid, which is suitable for sc or im administration, in a solution of a polypeptide.

The presentation forms of proteins to be used therapeutically are with a few exceptions limited to intravenous administration. Oral administration of polypeptides is in many cases unsuccessful, as the polypeptides are degraded in the gastrointestinal tract. It has already been attempted with the aid of various methods, for example by micro encapsulation in liposomes, to develop orally administrable presentation forms of polypeptides. Until now, however, these methods were only suitable for low molecular weight polypeptides.

It has therefore been attempted to administer the polypeptides sc or im. However, in this case it turns out that sc or im administration, in comparison to classical iv administration, offers a distinctly poorer bioavailability or can be affected by local intolerability reactions.

However, sc and im administration forms offer potentially important advantages in comparison to iv administration. Among these are included, in particular, the possibility of self-treatment for the patients and a longer-lasting action of the therapeutic.

In WO 86/06962 and EP-A-0,292,908, methods for sc or im administration of proteins in the presence of hydroxylamine or methylamine are described. However, it is known that these substances can only be used in a restricted manner owing to their limited tolerability.

The object of the present invention was therefore to make available an agent containing a polypeptide, which is suitable for sc or im administration.

BRIEF DESCRIPTION OF DRAWINGS

FIG. 1 is a graphical representation of t-PA-Mutant intramuscular administration in Buffers 1, 3, 5, and 7.

FIG. 2 is a graphical representation of t-PA-Mutant subcutaneous administration in Buffers 1, 3, 5, and 7.

This object is achieved according to the invention in that at least one amino acid, or a salt, derivative or homolog of an amino acid, is incorporated in the polypeptide-containing solution. Preferably, a D- or L-amino acid is incorporated.

It has surprisingly been shown that the addition of such a substance drastically improves the bioavailability and tolerability of polypeptides administered sc or im and thus makes possible their sc or im administration.

Substances suitable for the purpose according to the invention are, for example, lysine, ornithine, arginine, diaminopimelic acid, agmatine, creatinine, guanidino-acetic acid, acetylornithine, citrulline, arginino-succinic acid, tranexamic acid or epsilon-aminocaproic acid. A feature common to them all is the presence of a basic group in the form of an amino or guanidino group.

A particularly suitable combination has proved to be arginine and lysine, preferably 0.001 to 1 mol/l, particularly, preferably 0.01 to 0.5 mol/l. The bioavailability of polypeptides administered sc or im is distinctly increased by such an addition in comparison to a solution which contains the polypeptide and, if desired, customary additives such as stabilizers.

This favorable influence of these substances on the bioavailability and/or improvement in the tolerability could be observed particularly for t-PA (tissue plasminogen activator), a t-PA mutant, hirudin, urokinase, AT III (antithrombin III), factor XIII, EPO (erythropoietin), von Willebrand factor and PP4 (placenta protein 4). The activity of the proteins to which, according to the invention, the described substances were added is maintained even after lyophilization and dissolving before administration in sterilized water.

In an embodiment according to the invention, a procedure is used in which the polypeptide-containing solution is dialyzed against a buffer; for example a phosphate, trisglycine, acetate or citrate buffer, having a concentration of 0.001 to 0.1 mol/l, preferably of 0.01 to 0.05 mol/l, having a pH of 2 to 10, preferably of 4 to 9, containing at least one amino acid which can contain another amino group or a-guanidino group, or an amino acid derivative, for example lysine, ornithine, arginine, diaminopimelic acid, agmatine, creatinine, guanidino-acetic acid, acetylornithine, citrulline, arginino-succinic acid, tranexamic acid or epsilon-aminocaproic acid, preferably lysine, ornithine or arginine in a concentration of 0.005 to 0.5 mol/l, preferably of 0.01 to 0.3 mol/l, at a temperature of 2° to 30° C., preferably of 4° to 15° C.

The conductivity of the dialysis solution is preferably 1 to 50 mSi (20° C.), preferably 5 to 30 mSi (20° C.). The osmoeality is 10 to 2000 mOsmol, preferably 100 to 1000 mOsmol.

After completion of the dialysis, the polypeptide-containing solution is adjusted to the desired final concentration by concentration or dilution. The solution is then sterile filtered, bottled and, if desired, lyophilized.

The solutions according to the invention are equally suitable for use in human and veterinary medicine. As solely physiologically tolerable substances are added, neither inflammation nor skin irritation or vascular damage occurs in the administration of the solutions according to the invention.

Using the preparation forms according to the invention, it is now possible by means of sc or im administration to achieve plasma concentrations of polypeptides which make possible both prophylaxis and therapy.

The examples illustrate the invention.

EXAMPLE 1

Preparation of the protein solutions for sc and im administration 1. r-t-PA ($^R$Actilyse) was purchased from Boehringer Ingelheim.
2. Urokinase (UK) ($^R$Actosol) was obtained from Behringwerke. P0 3. F XIII ($^R$Fibrogammin) was obtained from Behringwerke.
4. Antithrombin III (AT III) ($^R$Kybernin) was obtained from Behringwerke.
5. r-Hirudin was prepared by the process of EP 0,316,650.
6. r-t-PA mutant (No. 1) was prepared by the process of EP 0,227,462.
7. von Willebrand (vW) was prepared by the process of DE 3,904,354 (1 mg of vW corresponds to 100 U of vW antigen).

8. PP4 was prepared by the process of EP 0,123,307.
9. r-erythropoietin (EPO) was prepared by the process of EP 0,123,307 (1 mg of EPO corresponds to 80,000 U of EPO antigen).

The proteins 1 to 4 were dissolved in distilled water. The proteins 1 to 9 were then dialyzed against the following buffers (Table 1).

| r-t-PA | ELISA | (Biopool, Sweden) |
| Urokinase | ELISA | (Biopool, Sweden) |
| F XIII: | Activity test | (Behringwerke) |
| Antithrombin III: | ELISA | (Behringwerke) |
| r-Hirudin: | ELISA | (Behringwerke) |

TABLE 1

| P** | Final concentration | t-t-PA 1* | r-t-PA-mutant 0.5* | Uro-kinase 3.1* | FXIII 5.5 mg | ATIII 8.3* | r-Hirudin 1.2* | vW 150 U/ml | PP4 5* | rEPO 200 U/ml |
|---|---|---|---|---|---|---|---|---|---|---|
| 1 | Dialysis against 0.05 M tris 0.1 M NaCl | x | x | x | x | x | x | x | x | x |
| 2 | idem pH 4.5 | x | x | | | | | | | |
| 3 | 0.2 M arginine 0.2 M lysine pH 7.5 | x | x | x | x | x | x | x | x | x |
| 4 | 0.2 M arginine 0.2 M lysine pH 4.5 | x | x | | | | | | | |
| 5 | 0.05 M tris (1) 0.1 M NaCl pH 7.5 0.1% Tween 80 50* hydroxylamine | x | x | | | | | | | |
| 6 | idem pH 4.5 | | x | | | | | | | |
| 7 | 0.05 M tris (1) *0.1 M NaCl pH 7.5 *0.1% Tween 80 3% dimethyl sulfoxide | x | x | | | | | | | |
| 8 | 0.2 M arginine pH 7.5 | x | | | | | | | | |
| 9 | 0.2 M lysine pH 7.5 | x | | | | | | | | |

(1) according to PNAS 82, 4258–4262 (1985); *mg/ml; **buffer

After the dialysis, the solutions obtained are sterile filtered and frozen at −20° C. until use.

EXAMPLE 2

Each ml of the thawed solutions from Example 1 was administered sc and im (femoral biceps) in animals (rats or rabbits). In the case of im administration, the total volume of 1 ml was divided between four types of injection.

The animals were treated as follows:

| | | Number of Animals | |
|---|---|---|---|
| Test Substance | Dose | Rats per group | Rabbits per group |
| r-t-PA | 3.3/8.2 mg/kg | 2 | 3 |
| Urokinase | 5 mg/kg | | 3 |
| F XIII | 10 mg/kg | | 3 |
| AT III | 10 mg/kg | | 3 |
| r-Hirudin | 10 mg/kg | 3 | |
| r-t-PA-mutant | 1.7 mg/kg | 2 | |
| von Willebrand | 300 U/kg | | 3 |
| PP4 | 10 mg/kg | 3 | |
| EPO | 2000 U/kg | | 3 |

After 0, 15, 30, 60, 120, 180, 240 and 340 minutes (r-t-PA mutant) or 0, 30, 60, 120, 180, 240, 300, 360, 420 and 450 minutes (r-t-PA, hirudin, urokinase AT III, F XIII, von Willebrand, EPO, PP4), blood samples (+ citrate) were taken. The blood samples were then immediately centrifuged and the resulting citrate plasma was frozen at −20° C. until the determination. The plasma concentration of the test substance was measured as follows:

| r-t-PA mutant | ELISA | (Biopool Sweden) |
| von Willebrand: | ELISA | (Stago, France) |
| PP4: | ELISA | (Behringwerke) |
| r-Erythropoietin: | ELISA | (Behringwerke) |

The data determined were represented graphically, as shown in FIGS. 1 and 2. The area under the curve (AUC) was then calculated. This value is an expression of the bioavailability and makes possible comparison between the different presentation forms. The data show that the administration of the solutions according to the invention, with the exception of urokinase and hirudin ensures a distinctly better bioavailability, in particular in the case of sc administration.

Surprisingly, it has been found that the hemorrhages occurring on sc and im administration of hirudin and of urokinase at the administration site using the presentation form according to the invention occur distinctly less than when these substances are administered in their customary presentation forms.

| Number of animals with hemorrhages | | | |
|---|---|---|---|
| | | im | sc |
| Hirudin | 0.05 M tris 0.1 M NaCl | 3/3 (1 animal died as a result of the hemorrhages) | 2/3 |
| Hirudin | 0.2 M arginine 0.2 M lysine pH 7.5 | 0/3 | 0/3 |
| Urokinase | 0.05 M tris 0.1 M NaCl pH 7.5 | 2/3 | 2/3 |

Number of animals with hemorrhages

| | | im | sc |
|---|---|---|---|
| Urokinase | 0.2 M arginine<br>0.2 M lysine<br>pH 7.5 | 1/3 | 0/3 |

I. Bioavailability of t-PA in the rat

| Buffer | Type of Administration | n | AUC + Variation (%) |
|---|---|---|---|
| 1 | im | 2 | 358 ± 10% |
|   | sc | 2 | 36 ± 13% |
| 2 | im | 2 | 386 ± 2% |
|   | sc | 2 | 53 ± 14% |
| 3 | im | 2 | 756 ± 2% |
|   | sc | 2 | 423 ± 3% |
| 4 | im | 2 | 669 ± 17% |
|   | sc | 2 | 382 ± 11% |
| 5 | im |   | (all animals died) |
|   | sc |   | (all animals died) |
| 7 | im | 2 | 184 ± 18% |
|   | sc | 2 | 87 ± 12% |
| 8 | im | 2 | 600 ± 4% |
|   | sc | 2 | 320 ± 2% |
| 9 | im | 2 | 610 ± 10% |
|   | sc | 2 | 290 ± 11% |

II. Bioavailability of t-PA mutant in the rat

| Buffer | Type of Administration | n | AUC + Variation (%) |
|---|---|---|---|
| 1 | im | 2 | 113 ± 2% |
|   | sc | 2 | 13 ± 20% |
| 2 | im | 2 | 295 ± 0.5% |
|   | sc | 2 | 161 ± 12% |
| 3 | im | 2 | 1524 ± 13% |
|   | sc | 2 | 1119 ± 14% |
| 4 | im | 2 | 1414 ± 2% |
|   | sc | 2 | 1277 ± 21% |
| 5 | im | 2 | 32 ± 5% |
|   | sc | 2 | 34 ± 10% |
| 6 | im |   | (all animals died directly after administration) |
|   | sc |   | (all animals died directly after administration) |
| 7 | im | 2 | 30 ± 12% |
|   | sc | 2 | 39 ± 9% |

III. Bioavailability of antithrombin III (rabbits)

| Buffer | Type of Administration | n | AUC + Variation (%) |
|---|---|---|---|
| 1 | im | 3 | 456,000 ± 28 |
|   | sc | 3 | 57,000 ± 19 |
| 3 | im | 3 | 601,000 ± 15 |
|   | sc | 3 | 116,400 ± 18 |

IV. Bioavailability of F XIII (rabbits)

| Buffer | Type of Administration | n | AUC + Variation (%) |
|---|---|---|---|
| 1 | im | 3 | 228,000 ± 25 |
|   | sc | 3 | 35,000 ± 12 |
| 3 | im | 3 | 60,600 ± 23 |
|   | sc | 3 | 62,000 ± 20 |

V. Bioavailability of von Willebrand factor (rabbits)

| Buffer | Type of Administration | n | AUC + Variation (%) |
|---|---|---|---|
| 1 | im | 3 | 231 ± 14 |
|   | sc | 3 | 61 ± 20 |
| 3 | im | 3 | 715 ± 16 |
|   | sc | 3 | 12 ± 14 |

I claim:

1. A pharmaceutical solution consisting essentially of erythropoietin and arginine or a salt thereof.

* * * * *